United States Patent
Wenstrom, Jr. et al.

(10) Patent No.: US 6,620,166 B1
(45) Date of Patent: *Sep. 16, 2003

(54) SUTURE BUTTRESS SYSTEM

(75) Inventors: Richard F. Wenstrom, Jr., Norwood, MA (US); Edward V. Craig, New Canaan, CT (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/004,989

(22) Filed: Jan. 9, 1998

(51) Int. Cl.$^7$ .............................................. A61B 17/56
(52) U.S. Cl. ...................... 606/72; 606/148; 606/232; 606/233
(58) Field of Search .................. 606/72, 73, 74, 606/75, 144, 148, 232, 233, 220

(56) References Cited

U.S. PATENT DOCUMENTS

| | | | |
|---|---|---|---|
| 3,845,772 A | 11/1974 | Smith | 128/335 |
| 4,009,719 A | 3/1977 | Kletschka et al. | 128/335 |
| 4,045,825 A | 9/1977 | Stroot | 3/1.91 |
| 4,549,545 A | 10/1985 | Levy | 128/335 |
| 4,632,100 A | 12/1986 | Somers et al. | |
| 4,738,255 A | 4/1988 | Goble et al. | |
| 4,894,063 A | 1/1990 | Nashef | |
| 5,224,946 A * | 7/1993 | Hayhurst et al. | 606/72 |
| 5,366,480 A | 11/1994 | Corriveau et al. | 606/233 |
| 5,423,763 A | 6/1995 | Helland et al. | 604/174 |
| 5,540,703 A | 7/1996 | Barker, Jr. et al. | |
| 5,575,801 A | 11/1996 | Habermeyer et al. | 606/148 |
| 5,632,748 A | 5/1997 | Beck, Jr. et al. | 606/89 |
| 5,681,333 A | 10/1997 | Burkhart et al. | 606/148 |
| 5,921,918 A * | 7/1999 | Riza | 600/24 |
| 6,156,056 A | 12/2000 | Kearns et al. | |
| 6,245,081 B1 | 6/2001 | Bowman et al. | |

FOREIGN PATENT DOCUMENTS

| | | |
|---|---|---|
| DE | 31 46634 A1 | 1/1983 |
| WO | WO 92/10149 | 6/1992 |
| WO | WO9806344 | 2/1998 |

OTHER PUBLICATIONS

Gerber, Christian et al. "Mechanical Strength of Repairs of The Rotator Cuff", The Journal of Bone And Joint Surgery, vol. 76–B, No. 3, (1994).

"Avoid suture migration following rotator cuff repair" *Cuff Link™*, Bone Tunnel Augmentation Device, Innovasive Devices, Inc., Copyright 1997.

*Innovasive Cuff Link™*, Bone Tunnel Augmentation Device, Instructions for Use, pp. 1–3.

The Rotator Cuff Repair System Surgical Technique, Surgical technique as described by Stephen J. Snyder, M.D., Southern California Orthopedic Institute, Vans Nuys, California.

* cited by examiner

*Primary Examiner*—Michael A. Brown
(74) *Attorney, Agent, or Firm*—Nutter, McClennen & Fish LLP

(57) ABSTRACT

A suture buttress system has a suture retriever and a suture buttress. The suture retriever includes a handle portion with an elongate member extending therefrom and having an outer surface and a distal end that includes a suture retaining element. The suture buttress comprises a resilient hollow tube having an outer surface and opposed ends. The suture buttress is removably and replaceably disposed on the elongate member. The suture buttress may further include an external fastening element suitable to retain the suture buttress within a bone tunnel. A suture buttress deployment tool may also be provided.

40 Claims, 5 Drawing Sheets

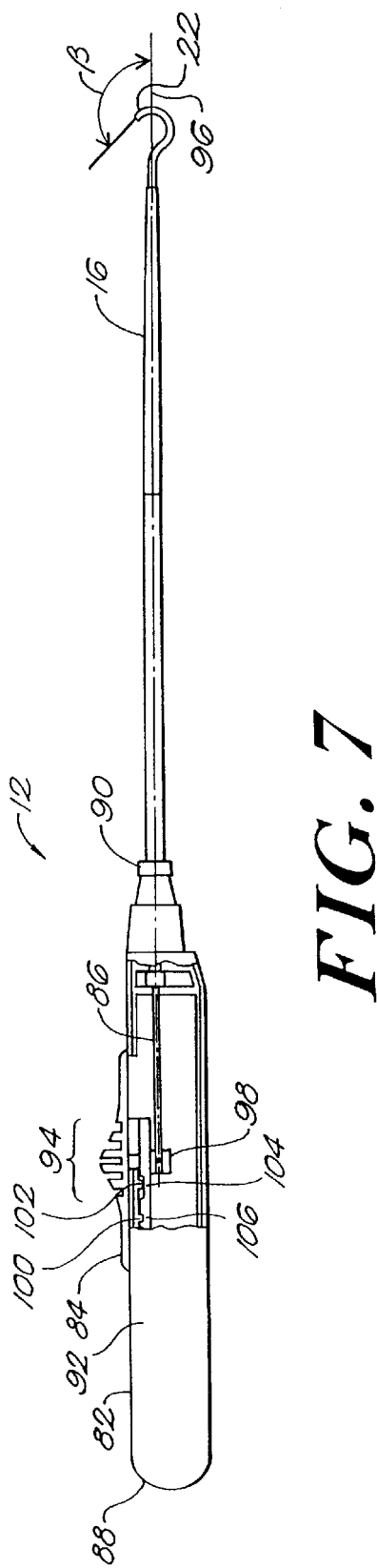
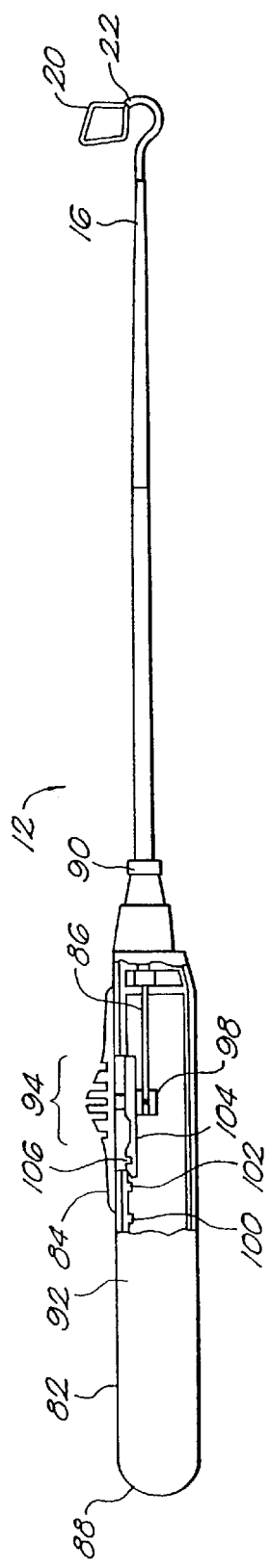
FIG. 7
FIG. 8

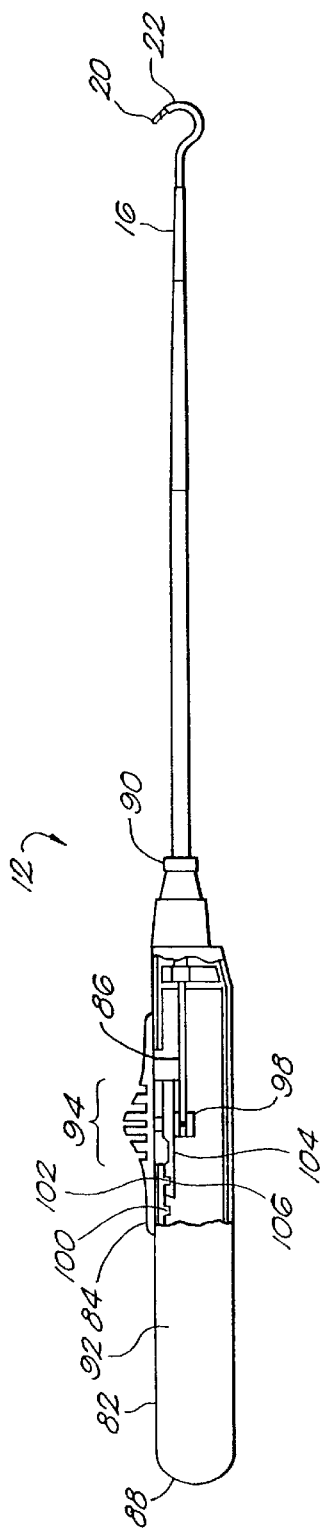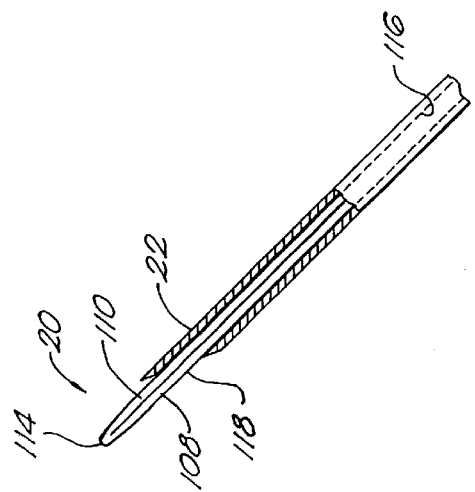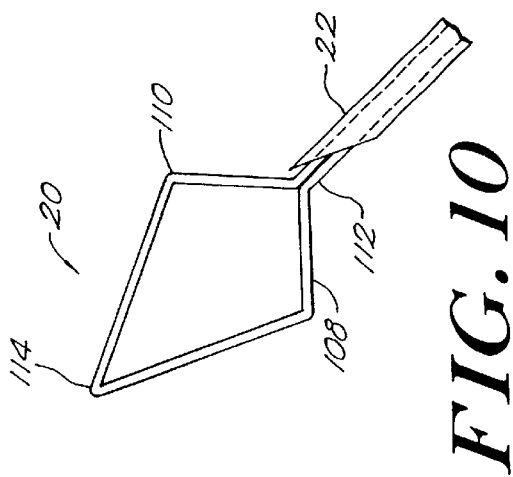

SUTURE BUTTRESS SYSTEM

CROSS-REFERENCE TO RELATED APPLICATIONS

Not Applicable.

STATEMENT REGARDING FEDERALLY SPONSORED RESEARCH

Not Applicable.

FIELD OF THE INVENTION

The invention relates to a suture buttress and a system for deploying the suture buttress and manipulating a suture.

BACKGROUND OF THE INVENTION

Open repair of the rotator cuff tendon is the most common open surgical procedure performed on the shoulder. It has been estimated that the incidence of rotator cuff tearing in the population at large runs between 15 and 25%, with approximately half of these being full thickness tears of the tendon. A smaller percentage of these become sufficiently symptomatic to warrant surgical repair.

Generally, techniques for repairing rotator cuff tears involve reattaching the torn tendon back to the bone from which it is avulsed. Typically, suture material is used to tie the tendon directly back to bone to facilitate healing of the tendon. Common technical problems with this repair often result from the fact that rotator cuff tears frequently occur in patients who are in an older age group. These patients often have poor quality bone, osteopenic bone, or bone that has been weakened by disuse due to pain. When the tendon is brought back to the bone, attempts to hold the tendon securely to the bone can be frustrated by the poor quality bone.

One method for reattaching the rotator cuff tendon to bone is to make a hole or tunnel in the bone of the greater tuberosity, to pass suture thread that has been secured to the tendon through these bone tunnels, and to reattach the rotator cuff tendon directly to the bone by tying these sutures. Using this method, the suture material can be frayed and weakened, or possibly severed, by contact with sharp edges of subcortical bone inside the bone tunnel or at the openings of the bone tunnel.

Poor bone quality also affects this method of repair adversely as the suture material may cut directly through the bone, frustrating the attempts at secure repair. Even where the suture does not cut completely through the bone, any amount of carving into bone by the suture material may result in a loosening of the suture and a corresponding loosening of the attachment of the rotator cuff tendon to bone.

SUMMARY OF THE INVENTION

The present invention provides a suture buttress system. The system of the invention has a suture retriever including a handle and an elongate member extending from the handle. The elongate member has an outer surface and a suture retaining element located at its distal end. The suture buttress system also includes a suture buttress composed of a resilient hollow tube having an outer surface and opposed ends. The suture buttress is removably and replaceably disposed on the elongate member of the suture retriever.

In one embodiment, the suture buttress includes an external fastening element made up of one or more slits formed in the outer surface of the suture buttress. The slits are formed at an angle to a plane transverse to a longitudinal axis of the suture buttress so that when the tube is flexed, such as when the tube is disposed on a curved portion of the suture retriever, at least one raised edge extends outward from the outer surface of the suture buttress. The slits may be angled so that the raised edges allow the suture buttress to slide into a bone tunnel in a first direction when urged into the tunnel by insertion of the suture retriever into the tunnel, but the raised edges engage the tunnel to prevent the suture buttress from sliding out of the tunnel in a direction opposite from the insertion direction.

Other external fastening elements useful with the suture buttress include resilient flanges disposed on the outer surface of the buttress and folding a portion of the tube adjacent to each of the opposed ends of the buttress over onto the outer surface of the buttress. A suture buttress deployment tool may also be removably and replaceably disposed on the outer surface of the suture retriever in proximity to the suture buttress.

The invention also provides a bone tunnel buttress. The bone tunnel buttress includes an elongate hollow tube having an outer surface and opposed proximal and distal ends. At least one external fastening member is formed on the outer surface of the tube. The bone tunnel buttress of the invention may be deployed within a bone tunnel so that the external fastening member prevents removal of the bone tunnel buttress from a bone tunnel in a direction opposite to a direction of insertion of the bone tunnel buttress.

BRIEF DESCRIPTION OF THE DRAWINGS

The invention will be more fully understood by reference to the following detailed description when considered in conjunction with the accompanying drawings, in which:

FIG. 7 is an elevated view, with a partial cut-away, of the suture retriever of FIG. 1, with the suture retaining element in a retracted position;

FIG. 8 is an elevated view, with a partial cut-away, of the suture retriever of FIG. 1, with the suture retaining element in an extended position;

FIG. 9 is an elevated view, with a partial cut-away, of the suture retriever of FIG. 1, with the suture retaining element in a partially retracted, intermediate position;

FIG. 10 is an elevated view of the suture retaining element of FIG. 1 in an extended position;

FIG. 11 is an elevated view, with a partial cut-away, of the suture retaining element of FIG. 1 in an intermediate position.

DETAILED DESCRIPTION OF THE INVENTION

Figure 1:
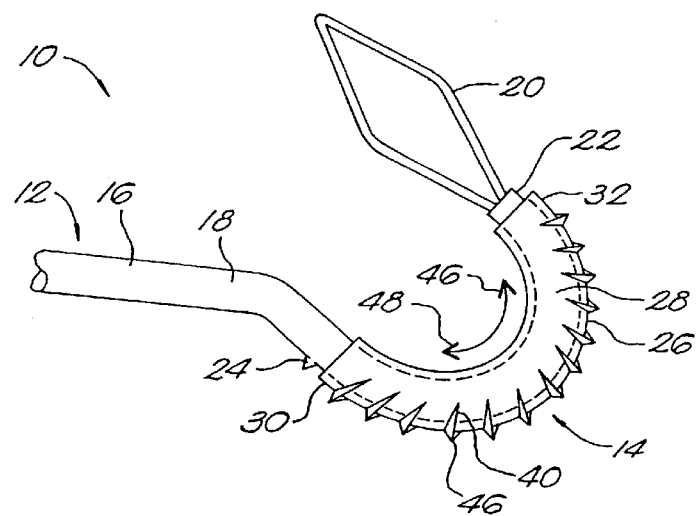
FIG. 1 is an elevated view of a suture buttress system showing a distal portion of a suture retriever, a suture buttress disposed on the retriever and a suture retaining element extending from the retriever.

An exemplary suture buttress system 10 of the invention, illustrated in FIG. 1, includes a suture retriever 12 and a suture buttress or bone tunnel buttress 14. The suture retriever 12 has an elongate portion 16 having an outer surface 18 and a suture retrieving element 20 disposed at its distal end 22. The suture buttress 14 is removably and replaceably disposed on the outer surface 18 of the elongate member 16. A suture buttress stop 24 may also be provided on the outer surface 18 of the elongate member 16 in proximity to the suture buttress 14.

Figure 2:
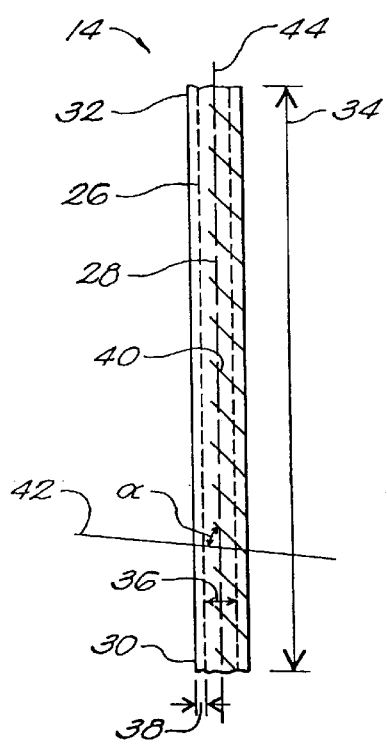
FIG. 2 is an elevated view of the suture buttress of FIG. 1 in an unflexed position.
Figure 3:
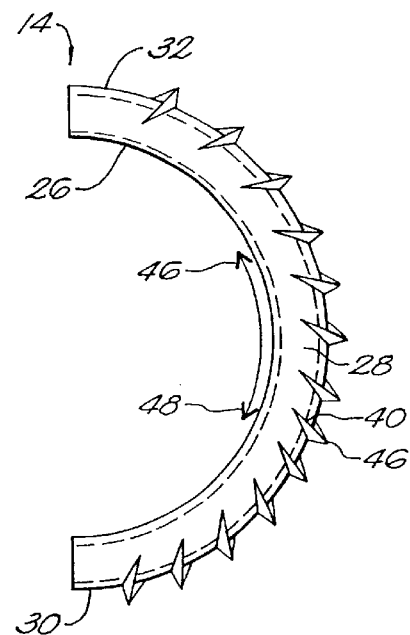
FIG. 3 is an elevated view of the suture buttress of FIG. 1 in a flexed position.

The suture buttress 14, illustrated in FIGS. 1–3, includes a resilient hollow tube 26 having an outer surface 28 and opposed proximal and distal ends 30, 32. The resilient hollow tube 26 may be made from a variety of resilient materials including absorbable and non-absorbable materials. Exemplary non-absorbable polymeric materials include polysulfone, PEEK, Nylon and Delrin. Exemplary bioabsorbable materials useful for making the resilient hollow tube 26 include homo and copolymers of glycolide and trimethylene carbonate, homo and copolymers of lactide and glycolide, homo and copolymers of polylactic acid, or a combination of these materials. Additionally, the resilient hollow tube 26 may be constructed from the same materials used to construct sutures for use in orthopedic procedures, including polydioxanone (PDS) and other materials known to those of ordinary skill in the art.

The resilient tube 26 should have sufficient length 34 to protect a suture as applied in surgical procedure and, in particular, in an orthopedic procedure where the suture is passed through a bone tunnel. Generally, where the suture buttress system 10 is used in rotator cuff repair surgery in which a suture is passed though a bone tunnel in the proximal humerus, the length 34 of the resilient tube should be between about 0.75 and 1.50 inches.

The inner diameter 36 of the resilient tube 26 should be large enough to allow the tube 26 to be removably and replaceably disposed on the outer surface 18 of the suture retriever 12 and large enough to allow a suture to be drawn through the tube 26. In addition, the inner diameter 36 must be selected so that, with an appropriate wall thickness 38, the resilient tube 26 will fit within a suitably sized bone tunnel. Generally, for use in rotator cuff repair surgery, the inner diameter 36 of the resilient tube 26 is between about 0.060 and 0.085 inches and the wall thickness 38 is between about 0.014 and 0.018 inches.

The resilient tube 26 may be provided with an external fastening element that is effective to secure it within a bone tunnel. The exemplary resilient tube 26 is provided with at least one angled slit 40 for this purpose. Each slit 40 is angled by an amount a with respect to a plane 42 that is transverse to a longitudinal axis 44 of the resilient tube 26. While the angle a may take on any value, $\alpha$ is preferably positive and more preferably is between about 20° and 60°. When the slits 40 are so angled, flexing the resilient tube (as shown in FIGS. 1 and 3) causes a series of raised edges 46 to extend outward from the outer surface 28 of the resilient tube 26. The edges 46 are angled so that they are easily deformed and pressed back to the outer surface 28 to allow the resilient tube 26 to slide into a bone tunnel when urged in a first direction 46 into the bone tunnel by a surgeon when inserting the suture retriever 12 into the tunnel.

The suture buttress stop 24, provided on the outer surface 18 of the elongate member 16 in proximity to the suture buttress 14, may prevent the resilient tube 26 from sliding backwards on the outer surface 18 of the elongate member 16 during insertion of the suture retriever 12 into a bone tunnel in the first direction 46. The suture buttress stop 24 may be formed by cutting out or otherwise deforming a portion of the outer surface 18 of the elongate member 16, by attachment to the outer surface 18, or in some other manner that may be selected by a person of ordinary skill in the art.

Once the resilient tube 26 has been inserted into a bone tunnel, the raised edges 46 engage the inner surface of the bone tunnel to prevent the resilient tube 26 from sliding out of the bone tunnel in a second direction 48, substantially opposed to the first direction 46, when the suture retriever 12 is removed from the bone tunnel. The suture buttress 14 is thus left in position within the bone tunnel as the suture retriever 12 is used to draw a suture through the suture buttress 14 and through the bone tunnel.

The slits 40 should be deep enough to cause the desired raised edges 46 when the resilient tube 26 is flexed, but not so deep as to compromise the structural integrity of the resilient tube 26. Otherwise, the depth of the slits 40 is not particularly limited and the slits 40 may have a depth that is less than the wall thickness 38 of the resilient tube 26, or the slits 40 may be deeper than the wall thickness 38 so that the slits 40 extend into the interior of the tube 26.

Figure 4:
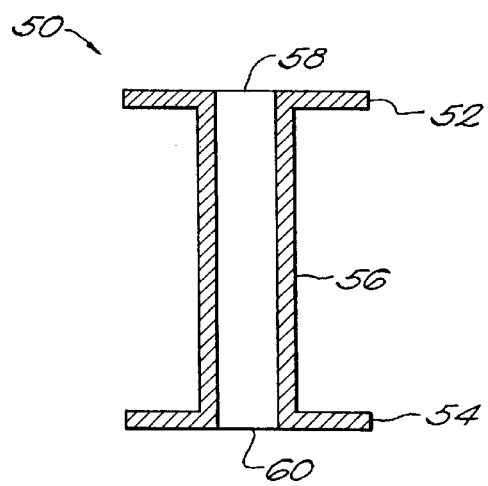
FIG. 4 is a cross-sectional view of a suture buttress having flanges.
Figure 5:
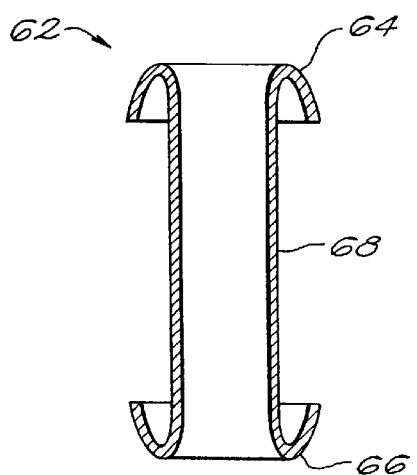
FIG. 5 is a cross-sectional view of a suture buttress having opposed ends folded over onto an outer surface of the buttress.

One of ordinary skill in the art will appreciate that a variety of other external fastening elements may be utilized to secure the suture buttress within a bone tunnel. Examples of suture buttresses having other external fastening elements are illustrated in FIGS. 4 and 5. Suture buttress 50 of FIG. 4 has a resilient hollow tube 51 with two resilient circumferential flanges 52, 54 formed on the outer surface 56 of resilient tube 51. One flange is formed adjacent to each of the opposed ends 58, 60 of the resilient tube 51. A person of ordinary skill in the art will appreciate that more or fewer flanges may be used and that the location of the flanges may be varied as necessary to achieve the purpose of the invention. The suture buttress 62, illustrated in FIG. 5, includes portions of the resilient hollow tube 63 adjacent to each of the opposed ends 64, 66 that are folded over onto outer surface 68 of the tube 63. The suture buttresses 50, 62 of FIGS. 4 and 5 may be applied using the suture retriever 12 illustrated in FIG. 1.

Figure 6:
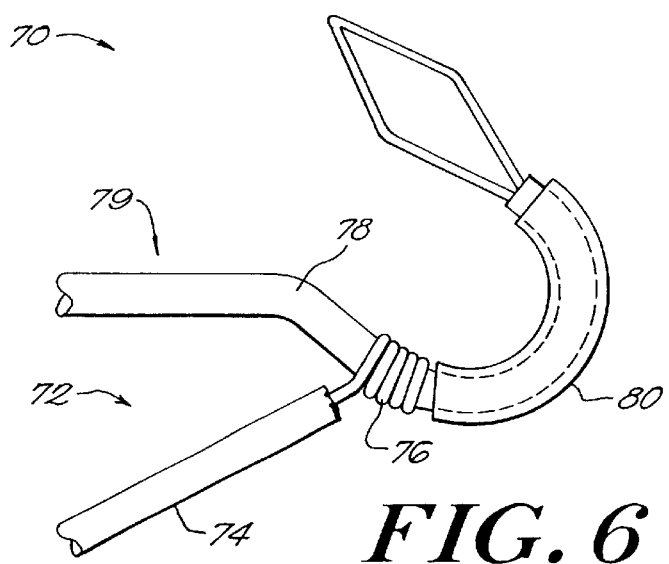
FIG. 6 is an elevated view of a suture buttress system including a suture buttress deployment tool.

A suture buttress system 70 may also include a suture buttress deployment tool 72 as illustrated in FIG. 6. The suture buttress deployment tool 72 has a handle 74 and a deployment element 76. The deployment element 76 may be removably and replaceably disposed on an outer surface 78 of the suture retriever 79 adjacent and proximal to a suture buttress 80. Because the suture buttress 80 can be deployed from the suture retriever using the deployment tool 72, the suture buttress 80 need not have an external fastening element. Also, because the deployment tool 72 may be used to urge the suture buttress 80 into a bone tunnel, it is not necessary to provide a suture buttress stop, such as the suture buttress stop 24 shown in FIG. 1, on the suture retriever 79.

The deployment element 76 of the suture buttress deployment tool 72 may be in the form of a partial or complete loop. In an embodiment in which the deployment element 76 is in the form of complete loop, the loop may be circular. Such a circular loop has an inner diameter large enough to slide over the outer surface 78 of the suture retriever 79. However, the inner diameter of the circular loop should be less than the outer diameter of the suture buttress 80 so that the circular loop can be used to push the suture buttress 80 off of the outer surface 78 of suture retriever 79.

The suture retrieving device 12 useful with the invention for retrieving or retrograding a suture or other ligature, is illustrated in FIGS. 7–11. This exemplary instrument includes a handle 82, an elongate member 16, a suture retaining element 20, an actuator 84 and a linking member 86 which connects the actuator 84 to the suture retaining element 20.

The exemplary handle 82 is elongate, generally cylindrical and has opposed proximal 88 and distal 90 ends. The shape and dimensions of the handle 82 may be selected by a person of ordinary skill in the art to allow the handle 82 to be suitably grasped by a surgeon in an operating environment.

The actuator 84 is slidably mounted on a side wall 92 of the handle 82. In the embodiment shown, the actuator 84 is rectangularly-shaped and includes a series of flanges 94 having varying heights and angled surfaces so as to be easily manipulated in either of two directions by a surgeon's thumb. The actuator 84 is mounted so as to slide in a direction substantially parallel to a longitudinal axis 96 of the suture retriever 12 and is movable between a first position (shown in FIG. 7), wherein the actuator 84 is closest to the proximal end 88 of the handle 82, and a second position (shown in FIG. 8), wherein the actuator 84 is closest to the distal end 90 of the handle 82. The actuator 84 may also be selectively positionable at an intermediate location between the first and second positions as illustrated in FIG. 9.

The actuator 84 communicates with the interior of the handle 82 through a transverse member 98. The transverse member 98 may extend through a rectangular slot (not shown) in the side wall 92 of the handle 82 along which the actuator 84 slides.

The transverse member 98 of the actuator 84 is connected to the linking member 86, which may be a rigid or semi-rigid rod. Preferably, the linking member 86 extends from the transverse member 98 in the interior of the handle 82 through the interior of the elongate member 16 to communicate with the suture retaining element 20.

Detents may be provided to lock the suture retriever 12 in the fully retracted and intermediate positions. These detents may suitably be provided by forming protuberances 100, 102 on the interior of the handle 82 corresponding to the fully retracted and intermediate positions respectively. A biased member 104 attached to the transverse member 98 of the actuator 84 has a recess 106 which corresponds to the shape of the protuberances 100, 102. Accordingly, when the actuator 84 passes into the first or intermediate position, a detent is achieved.

The distal end 22 of the elongate member 16 may extend at various angles and with various curvatures. For example, the distal end 22 of the elongate member 16 is curved and sweeps though an arc of approximately 180°. The suture retaining element 20 extends at an angle β that is approximately 135° with respect to the longitudinal axis 96 of the suture retriever 12. The distal end 22 of the elongate member 16 may also take on other configurations which may be selected by a person of ordinary skill in the art for the intended use of the suture retriever 12.

The suture retaining element 20 may be made from any flexible material suitable for surgical use including metals such as stainless steel or super elastic nickel-titanium (NITINOL), or plastic materials having elastic properties such as polyester, polypropylene or nylon. The suture retaining element 20 may be formed into a wire loop from a single, continuous wire element, or it may be formed using two wire elements joined at a distal portion of each.

The suture retaining element 20, illustrated in its extended position in FIG. 8, has two leg segments 108, 110. Beginning at a proximal end 112 of the suture retaining element 20 and moving distally, the leg segments 108, 110 diverge from one another, reach a point of maximum width therebetween, then converge to meet at a distal end 114 of the suture retaining element 20. The suture retaining element 20 thereby takes on a quadrangular or diamond shape when extended. In its extended position, the suture retaining element 20 has a maximum width between the leg segments 108, 110 in the range of approximately 0.100 to 0.800 inch, and more preferably about 0.400 inch.

The suture retaining element 20 may also be retracted to an intermediate position as shown in FIG. 11. As the actuator 84 is moved from its second or distal-most position to the intermediate position, the diverging portions of the two leg segments 108, 110 contact the inner wall 116 of the distal end 22 of the elongate member 16. This causes the quadrangular shaped wire loop suture retaining member 20 to compress, or fold up, as it is retracted into the elongate member 16. When the actuator 84 reaches the intermediate position, a small portion of the suture retaining element 20 remains extended beyond the distal end 11 of the elongate member 16 and thereby defines a region 118 within the suture retaining member 20 where a suture may be retained. The retained suture may then be drawn through a suture buttress 14 by the suture retriever 12. In this partially retracted position, the width of the suture retaining element 20 should be sufficient to slidably retain a suture within the suture retaining element 20. This width is generally in the range of about 0.020 to 0.250 inch, and more preferably is approximately 0.0675 inch. In this position, the suture retaining element may generally extend approximately 0.0675 to 0.250 inch, and more preferably extends about 0.125 inch from the distal end 22 of the elongate member 16.

Moving the actuator 84 to its first, proximal-most position fully retracts the suture retaining element 20 within the distal end 22 of the elongate member 16 as shown in FIG. 7.

The suture retaining device of the invention may utilize other suture retaining element configurations, such as a two-jaw suture retaining element or a suture retaining element consisting of two wire-like members. Examples of suture retaining elements known in the art may be found, for example, in U.S. Pat. Nos. 4,779,616; 5,250,054; 5,364,410; 5,499,991; 5,501,692; 5,562,685; 5,569,269 and 5,573,542.

Figure 12:
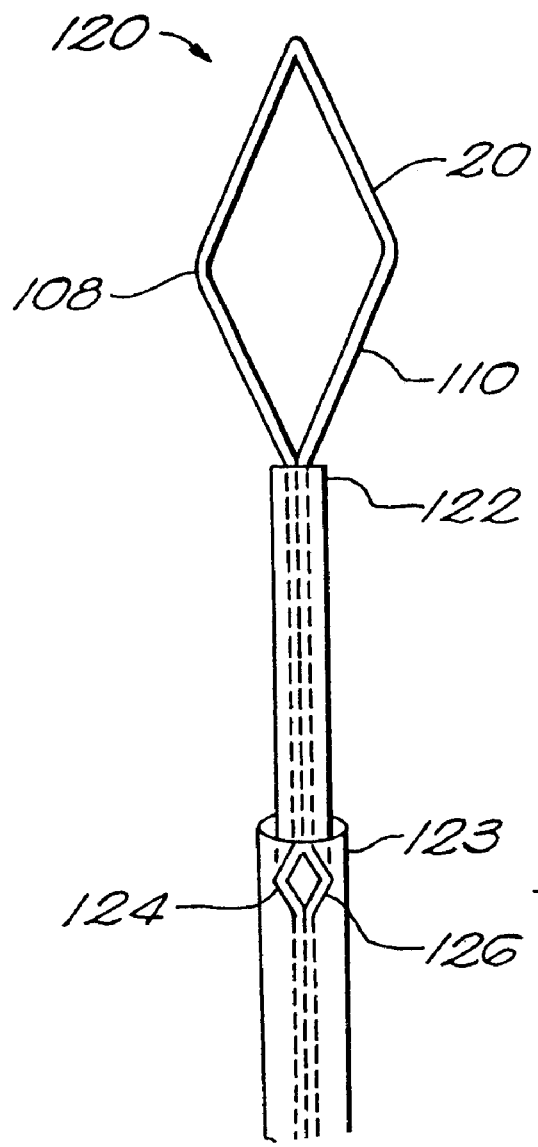
FIG. 12 is an elevated view of a suture tunnel buttress system having an internal tube delivery scheme.

An additional suture buttress system 120 having an internal tube delivery scheme is illustrated in FIG. 12. The suture buttress system 120 includes a suture buttress 122 that is at least partially disposed inside the distal end 123 of the elongate member of a suture retriever. In this embodiment, the leg portions 108, 110 extend proximally through the suture buttress 122 and form buttress deployment elements 124, 126 which push the suture buttress 122 out from its position inside the distal portion 123 and into a bone tunnel. External fastening elements, as described above, may be provided on the suture buttress 122 to retain it within the bone tunnel.

The suture buttress system may be employed in a variety of surgical applications, particularly those using a bone tunnel to attach soft tissue to a bone using one or more sutures. An exemplary procedure for using the suture buttress system with a bone tunnel begins with the step of preparing the soft tissue to be attached to the bone by resecting damaged portions and attaching at least one suture thread to the tissue.

A bone tunnel is then formed in proximity to the anatomic attachment point of the soft tissue to the bone. The tunnel is formed by piercing the cortical bone tissue at each end of the tunnel using a device such as a cortical bone punch or a drill. A circular bone rasp may be used to complete the tunnel through subcortical bone. The rasp may have teeth that can be used to smooth, to the extent possible, the subcortical bone and sharp cortical bone edges.

A suture buttress system, such as suture buttress system 10 illustrated in FIG. 1, is inserted, distal end 22 first and with the suture retaining element 20 retracted, into the end of the bone tunnel opposite the soft tissue. The suture buttress system 10 is inserted until the suture buttress 14 is fully disposed within the bone tunnel and the distal end 22 of the suture retriever 16 reaches the opposite end of the tunnel. The suture retaining element 20 is used to grasp a suture by extending the suture retaining element 20 and directing the suture therethrough. The suture retaining element 20 is then retracted to its intermediate or retracted position as appropriate to slidingly engage or snugly engage the suture. The suture retriever 16 is then removed from the bone tunnel so as to draw the suture through the tunnel and the suture buttress 14 while leaving the suture buttress 14 in place within the tunnel. The suture is then secured in any manner known to one of ordinary skill in the art in order to secure the soft tissue to the bone.

This procedure is particularly useful reattaching an injured rotator cuff tendon to the proximal humerus, however, a person of ordinary skill in the art will be able to apply the system, buttress and procedure of the invention in a variety of surgical situations.

It will be understood that the foregoing is only illustrative of the principles of the invention, and that various modifications can be made by those skilled in the art without departing form the scope and spirit of the invention. All references cited herein are expressly incorporated by reference in their entirety.

What is claimed is:

1. A suture buttress system, comprising:
   a suture retriever including a handle portion with an elongate member extending therefrom, the elongate member having an outer surface and a distal end that includes a suture retaining element; and
   a suture buttress comprising a resilient hollow tube having an outer surface and opposed proximal and distal ends, the suture buttress being removably and replaceably disposed on the elongate member such that when the suture retaining element extends beyond the distal end of the suture buttress, the sutress buttress retaining element is operable through the distal end of the hollow tube.

2. The system of claim 1, wherein the suture buttress further comprises an external fastening element extending from the outer surface thereof.

3. The system of claim 2, wherein the elongate member has a curved portion in proximity to its distal end.

4. The system of claim 3, wherein the suture buttress is removably and replaceably disposed on the outer surface of the curved portion of the elongate member.

5. The system of claim 4, wherein the external fastening element comprises at least one slit formed in at least a portion of the outer surface of the tube, the at least one slit being formed at an angle to a plane transverse to a longitudinal axis of the tube such that when the tube is flexed, a raised edge extends outward from the outer surface of the suture buttress.

6. The system of claim 5, wherein a plurality of slits are formed in the tube and each slit is angled in the same direction.

7. The system of claim 5, wherein the external fastening element is formed so as to allow the suture buttress to slide into a bone tunnel in a first direction when urged into the tunnel by insertion of the suture retriever into the tunnel, but the external fastening element engages the tunnel to prevent the suture buttress from sliding out of the tunnel in a second direction, substantially opposed to the first direction, when the suture retriever is removed form the tunnel.

8. The system of claim 2, wherein the external fastening element comprises at least one resilient flange located on the outer surface of the suture buttress.

9. The system of claim 8, wherein the external fastening element comprises two resilient flanges disposed on the outer surface of the suture buttress, wherein one flange is in proximity to each of the opposed ends of the suture buttress.

10. The system of claim 2, wherein the external fastening element comprises a portion of the resilient tube of the suture buttress adjacent one of the opposed ends, the portion being folded over onto the outer surface of the resilient tube.

11. The system of claim 10, wherein the external fastening element comprises a portion of the resilient tube from each of the opposed ends, each portion being folded over onto the outer surface of the resilient tube.

12. The system of claim 1, wherein the suture buttress is constructed from a resorbable material.

13. The system of claim 1, wherein the suture buttress has a length of between about 0.75 and 1.50 inches.

14. The system of claim 1, wherein the suture buttress has an inner diameter of between about 0.060 and 0.085 and a wall thickness of between about 0.014 and 0.018 inches.

15. The system of claim 1, further comprising a suture buttress deployment tool having a handle and a deployment element attached to a distal end of the handle, the deployment element being removably and replaceably disposed on the outer surface of the elongate member of the suture retriever proximal to the suture buttress.

16. The system of claim 15, wherein the deployment element is effective to deploy the suture buttress away from the outer surface of the elongate member within a bone tunnel.

17. The system of claim 15, wherein the deployment element comprises a circular member disposed around the elongate member of the suture retriever.

18. A bone tunnel buttress system, comprising:
   a suture retriever including a handle portion with an elongate member extending therefrom, the elongate member having an outer surface and a distal end that includes a suture retaining element; and
   a bone tunnel buttress comprising a resilient hollow tube with an outer surface and opposed proximal and distal ends, the bone tunnel buttress being removably and replaceably disposed on the elongate member such that the suture retaining element is operable through the distal end of the hollow tube, the bone tunnel buttress further including at least one external fastening element on the outer surface, the external fastening element being effective to allow the bone tunnel buttress to slide into a bone tunnel in a first direction when urged into the bone tunnel by the suture retriever while preventing the bone tunnel buttress from sliding out of the bone tunnel in a second direction that is substantially opposed to the first direction upon removal of the suture retriever from the bone tunnel.

19. The system of claim 18, wherein the external fastening element comprises at least one slit formed in at least a portion of the outer surface of the tube at an angle to a plane transverse to a longitudinal axis of the tube such that when the tube is flexed, a raised edge extends outward from the outer surface of the bone tunnel buttress.

20. The system of claim 19, wherein a plurality of slits are formed in the tube and each slit is angled in the same direction.

21. The system of claim 18, wherein the external fastening element comprises at least one resilient flange located on the outer surface of the bone tunnel buttress.

22. The system of claim 18, wherein the external fastening element comprises a portion of the resilient tube of the bone tunnel buttress adjacent one of the opposed ends, the portion being folded over onto the outer surface of the resilient tube.

23. The system of claim 18, wherein the bone tunnel buttress is constructed from a resorbable material.

24. The system of claim 18, wherein the bone tunnel buttress has a length of between about 0.75 and 1.50 inches.

25. The system of claim 18, wherein the bone tunnel buttress has an inner diameter of between about 0.060 and 0.085 inches and a wall thickness of between about 0.014 and 0.018 inches.

26. A bone tunnel buttress, comprising:
    a bioimplantable elongate hollow tube having an outer surface and opposed proximal and distal ends;
    at least one external fastening member formed on the outer surface of the tube, the bone tunnel buttress being effective for deployment within a bone tunnel such that the external fastening member prevents removal of the bone tunnel buttress from the bone tunnel in a direction opposite to a direction of insertion of the bone tunnel buttress within the bone tunnel; and
    wherein the external fastening element comprises at least one slit formed in at least a portion of the outer surface of the tube, the at least one slit being formed at an angle other than 90 degrees to a plane transverse to a longitudinal axis of the tube such that when the tube is flexed, a raised edge extends outward from the outer surface of the bone tunnel buttress.

27. The bone tunnel buttress of claim 26, wherein a plurality of slits are formed in the tube and each slit is angled in the same direction.

28. The bone tunnel buttress of claim 26, wherein the external fastening element is formed so as to allow the bone tunnel buttress to slide into a bone tunnel in a first direction when urged into the tunnel by insertion of the suture retriever into the tunnel, but the external fastening element engages the tunnel to prevent the bone tunnel buttress from sliding out of the tunnel in a second direction, substantially opposed to the first direction, when the suture retriever is removed form the tunnel.

29. The bone tunnel buttress of claim 26, wherein the external fastening element comprises at least one resilient flange located on the outer surface of the bone tunnel buttress.

30. The bone tunnel buttress of claim 29, wherein the external fastening element comprises two resilient flanges disposed on the outer surface of the bone tunnel buttress, one flange in proximity to each of the opposed ends of the bone tunnel buttress.

31. The bone tunnel buttress of claim 26, wherein the external fastening element comprises a portion of the resilient tube of the bone tunnel buttress adjacent one of the opposed ends, the portion being folded over onto the outer surface of the resilient tube.

32. The bone tunnel buttress of claim 31, wherein the external fastening element comprises a portion of the resilient tube from each of the opposed ends, each portion being folded over onto the outer surface of the resilient tube.

33. The bone tunnel buttress of claim 26, wherein the bone tunnel buttress is constructed from a resorbable material.

34. The bone tunnel buttress of claim 26, wherein the bone tunnel buttress has a length of between about 0.75 and 1.50 inches.

35. The bone tunnel buttress of claim 26, wherein the bone tunnel buttress has an inner diameter of between about 0.060 and 0.085 inches and a wall thickness of between about 0.014 and 0.018 inches.

36. A method for attaching soft tissue to a bone comprising the steps of:
    forming a first hole at least through cortical bone tissue of the bone proximate to the soft tissue attachment site;
    forming a second hole at least through cortical bone tissue of the bone spaced a predetermined distance apart from the first hole;
    connecting the first hole and the second hole though subcortical bone tissue to form a tunnel in the bone;
    attaching a suture thread to the soft tissue to be attached;
    providing a suture buttress system comprising:
        a suture retriever including a handle portion with an elongate member extending therefrom, the elongate member having an outer surface and a distal end that includes a suture retaining element; and
        a suture buttress comprising a resilient hollow tube having an outer surface and opposed ends, the suture buttress being removably and replaceably disposed on the elongate member;
    inserting the distal end of the elongate member of the suture buttress system into the second hole at least until the distal end of the elongate member reaches the first hole;
    engaging a suture attached to the soft tissue with the suture retaining element; and
    removing the suture retriever from the bone tunnel so as to draw the suture through the bone tunnel and the suture buttress while leaving the suture buttress within the tunnel.

37. The method of claim 36, wherein the first hole and the second hole are formed using a drill.

38. The method of claim 36, wherein the suture buttress further comprises at least one external fastening member formed on the outer surface of the tube, the bone tunnel buttress being effective for deployment within a bone tunnel such that the external fastening member prevents removal of the bone tunnel buttress from the bone tunnel in a direction opposite to a direction of insertion of the bone tunnel buttress within the bone tunnel.

39. The method of claim 38, wherein the bone tunnel is formed using a circular bone rasp.

40. The method of claim 39, wherein the external fastening element comprises at least one slit formed in at least a portion of the outer surface of the tube, the at least one slit being formed at an angle to a plane transverse to a longitudinal axis of the tube such that when the tube is flexed, a raised edge extends outward from the outer surface of the bone tunnel buttress.

* * * * *